(12) United States Patent
Kirsch

(10) Patent No.: US 10,165,348 B2
(45) Date of Patent: Dec. 25, 2018

(54) ADJUSTABLE OPENING HEADPHONES

(71) Applicant: Harman International Industries, Inc., Stamford, CT (US)

(72) Inventor: James Kirsch, Salt Lake City, UT (US)

(73) Assignee: Harman International Industries, Incorporated, Stamford, CT (US)

( * ) Notice: Subject to any disclaimer, the term of this patent is extended or adjusted under 35 U.S.C. 154(b) by 0 days.

(21) Appl. No.: 15/141,488

(22) Filed: Apr. 28, 2016

(65) Prior Publication Data

US 2016/0323664 A1     Nov. 3, 2016

Related U.S. Application Data

(60) Provisional application No. 62/154,552, filed on Apr. 29, 2015.

(51) Int. Cl.
| | |
|---|---|
| *A61F 11/14* | (2006.01) |
| *H04R 1/10* | (2006.01) |
| *H04R 3/04* | (2006.01) |
| *H04R 1/28* | (2006.01) |

(52) U.S. Cl.
CPC ............ *H04R 1/1041* (2013.01); *A61F 11/14* (2013.01); *H04R 1/1008* (2013.01); *H04R 3/04* (2013.01); *A61F 2011/145* (2013.01); *H04R 1/1083* (2013.01); *H04R 1/2826* (2013.01); *H04R 2420/07* (2013.01)

(58) Field of Classification Search
CPC ...... H04R 1/1041; H04R 1/1008; H04R 3/04; H04R 1/1083; H04R 2420/07; H04R 1/2826; A61F 11/14; A61F 2011/14

USPC ... 381/74, 373, 371, 370, 182, 150, 72, 103, 381/98
See application file for complete search history.

(56) References Cited

U.S. PATENT DOCUMENTS

| | | | | |
|---|---|---|---|---|
| 5,135,007 | A | * | 8/1992 | Lo ........................... A61F 11/14 128/846 |
| 5,844,998 | A | * | 12/1998 | Nageno ................ H04R 1/2842 381/371 |
| RE37,398 | E | * | 10/2001 | Nageno .................. H04R 5/033 381/370 |

(Continued)

OTHER PUBLICATIONS

European Search Report for corresponding application EP 16167202.7; dated Aug. 30, 2016; 8 pages.

*Primary Examiner* — Vivian Chin
*Assistant Examiner* — Con P Tran
(74) *Attorney, Agent, or Firm* — Brooks Kushman P.C.

(57) ABSTRACT

A headphone and method are provided. The headphone includes a headphone housing and a resilient cushion attached to the housing to define a chamber with the housing for enclosing the user's ear. An assembly is disposed in the housing proximate to a distal end and has a plurality of blades moveable between at least one open position and a closed position. In the closed position, the blades define a distal surface of the housing. In the open position, the assembly defines an aperture in the housing. The aperture allows sound communication from outside the housing into the chamber. The headphone is in communication with at least one external device and is programmed to receive a signal from the external device. The assembly to moves between the open position and the closed position based on the signal.

20 Claims, 6 Drawing Sheets

(56) References Cited

U.S. PATENT DOCUMENTS

| | | | |
|---|---|---|---|
| 6,549,635 B1 * | 4/2003 | Gebert | H04R 25/456 381/322 |
| 2005/0105755 A1 | 5/2005 | Yeuh | |
| 2007/0019820 A1 * | 1/2007 | Zurek | H04M 1/605 381/77 |
| 2010/0272303 A1 | 10/2010 | Lin | |
| 2012/0207320 A1 | 8/2012 | Avital | |
| 2015/0025662 A1 | 1/2015 | Di Censo et al. | |
| 2015/0036834 A1 * | 2/2015 | Bauman | H04R 1/1083 381/72 |
| 2015/0092976 A1 | 4/2015 | Kirsch et al. | |
| 2015/0110285 A1 | 4/2015 | Di Censo et al. | |
| 2015/0281827 A1 | 10/2015 | Burgett et al. | |

* cited by examiner

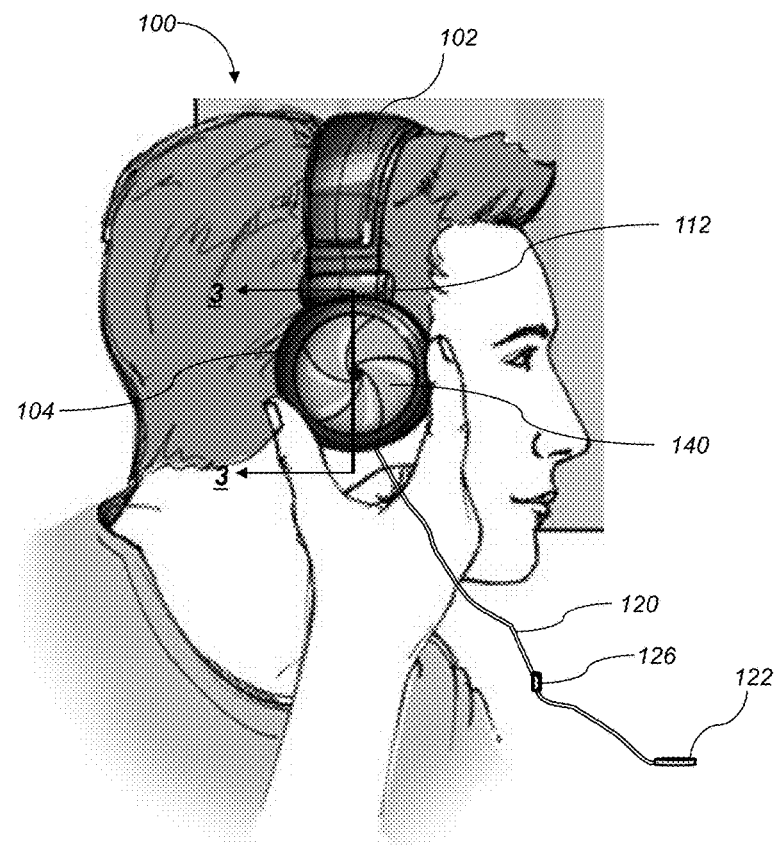
Fig. 1
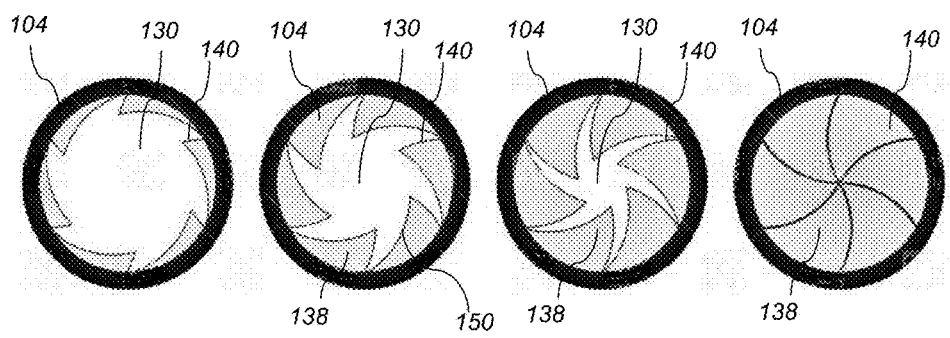
Fig. 2a  Fig. 2b  Fig. 2c  Fig. 2d

ADJUSTABLE OPENING HEADPHONES

CROSS-REFERENCE TO RELATED APPLICATIONS

This application claims the benefit of U.S. provisional application Ser. No. 62/154,552 filed Apr. 29, 2015, the disclosure of which is hereby incorporated in its entirety by reference herein.

TECHNICAL FIELD

The present disclosure generally relates to headphones such as audio headphones and hearing protectors.

BACKGROUND

Headphones typically include a resilient seal adapted to surround the user's ear. This type of headphone protects the wearer's ears from the surrounding environment's noise and conditions.

SUMMARY

According to at least one embodiment, a headphone is provided. The headphone includes a headphone housing and a resilient cushion attached to the housing to define a chamber with the housing for enclosing the user's ear. An assembly is disposed in the housing proximate to a distal end and has a plurality of blades moveable between at least one open position and a closed position. In the closed position, the blades define a distal surface of the housing. In the open position, the assembly defines an aperture in the housing. The aperture allows sound communication from outside the housing into the chamber. A controller is in communication with the assembly and at least one external device and is programmed to receive a signal from the external device. The controller commands the assembly to move between the open position and the closed position based on the signal.

In one embodiment, the external device includes a gun and the signal is indicative that the user is going to fire the gun, wherein the controller moves the assembly to the closed position before the user fires the gun.

In another embodiment, the headphone includes at least one acoustic driver for transmitting sound signals to the chamber in the headphone.

In one other embodiment, the controller includes an equalizer in communication with the acoustic driver. The equalizer increases low frequency sound signals when the assembly is in the open position.

In another embodiment, the external device includes a phone and the signal is indicative of an incoming call, wherein the controller moves the assembly to the closed position and turns off the acoustic driver.

In yet another embodiment, the headphone includes an actuator connected to assembly for moving the assembly between the open and closed position.

In another embodiment, the actuator comprises an electric motor connected to the assembly.

In still another embodiment, the assembly includes a rotating disk connected to housing and the blades. Rotation of the disk with respect to the housing moves the assembly between the open and closed position.

According to one other embodiment, the external device comprises a microphone and the signal is indicative of an alarm, wherein the controller moves the assembly to the open position before the user fires the gun.

According to at least one embodiment, a method is provided. The method includes providing a headphone housing having an assembly having a plurality of blades moveable between at least one open position and a closed position. In the closed position, the blades define a distal surface of the housing. In the open position, the assembly defines an aperture in the housing that allows sound communication from outside the housing into the chamber. The method includes receiving a signal from an external device. Based on the signal, the assembly moves between the open position and closed position In another embodiment, the method includes moving the assembly to the closed position when the signal is indicative that the user is going to fire a gun.

In one other embodiment, the method includes receiving a signal from a sensor disposed on a trigger of the gun.

In another embodiment, the method includes moving the assembly to the closed position when the signal is indicative of an incoming call.

In yet another embodiment, the method includes increasing low frequency sound signals by an acoustic driver via an equalizing filter when the assembly is in the open position.

In still another embodiment, the method includes providing an instruction to an actuator connected to assembly to moving the assembly between the open and closed position.

In another embodiment, the method includes moving the assembly to the open position when the signal is indicative of an alarm.

According to at least one embodiment, a headphone is provided having a headphone housing and a resilient cushion attached to the housing defining a chamber with the housing for enclosing the user's ear. An assembly is disposed in the housing proximate to a distal end and has a plurality of blades moveable between at least one open position and a closed position. In the closed position, the blades define a distal surface of the housing. In the open position, the assembly defines an aperture in the housing. The aperture allows sound communication from outside the housing into the chamber.

In another embodiment, the headphone includes a handle operable by the user outside the housing for moving the assembly between the open and closed position.

In one other embodiment, the assembly includes a rotating disk connected to handle and the blades. Rotation of the disk with respect to the housing moves the assembly between the open and closed position. Operation of the handle moves the rotating disk.

According to at least one embodiment, an audio listening device is provided. The listening device includes a first headphone cup and a second headphone cup, connected by a headband. Each of the first and second headphone cups has disposed on an exterior surface an aperture. Each aperture is configured to be open in a first state and closed in a second state, whereby in the first state an interior diaphragm of the headphone is exposed to an outside environment and whereby in the second state the interior diaphragm of the headphone is isolated from the outside environment.

According to at least one embodiment, an audio device is provided. The audio device includes a headset form communicating electronically with a plurality of electronic devices. The headset selectively prioritizes audio communicated by the electronic devices.

According to at least one embodiment, an earphone set, is provided. The earphone set includes a first earphone and a second earphone, each of the first and second earphones each able to be connected to communicate with an audio device wirelessly in a first mode. A cord is connected to each earphone at a disconnectable junction. The first and second earphone are each able to be connected to communicate with the audio device via the cord in a second mode.

According to at least one embodiment, an audio device is provided. The audio device includes a headphone set having a first and second earphone connected via a headband. The first earphone has a removable ear bud insertibly connected thereto. The ear bud is able to serve as a wireless audio device when disconnected from the first earphone.

BRIEF DESCRIPTION OF THE DRAWINGS

FIG. 1 illustrates a perspective view of headphones according to one embodiment, where the headphones are being worn by a user.

FIG. 2a illustrates a portion of the headphones shown in FIG. 1, where a headphone aperture is in an opened position.

FIG. 2b illustrates a portion of the headphones shown in FIG. 1, where the headphone aperture is in a partially opened position.

FIG. 2c illustrates a portion of the headphones shown in FIG. 1, where the headphone aperture is in a partially closed position.

FIG. 2d illustrates a portion of the headphones shown in FIG. 1, where the headphone aperture is in a closed position.

DETAILED DESCRIPTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

With reference now to FIG. 1, headphones 100 according to various aspects include two ear piece housings 104 connected by a support member 102. The support member 102 can rest on a wearer's head to support the weight of the ear piece housings 104. In various embodiments, the support member 102 could be shaped so that the ear piece housings 104 are touching or in close proximity to each other when the headphones 100 are not being worn.

To put on the headphones, a wearer would pull the ear piece housings 104 apart, resulting in the support member 102 applying a biasing force to the ear piece housings 104 that urges the ear piece housings 104 toward each other. The biasing force can press the ear piece housings 104 against the ears of the wearer to hold the headphones 100 in place on the wearer's head. In such instances, the support member 102 could rest on top of the wearer's head or behind the wearer's head, for example.

Figure 3A:
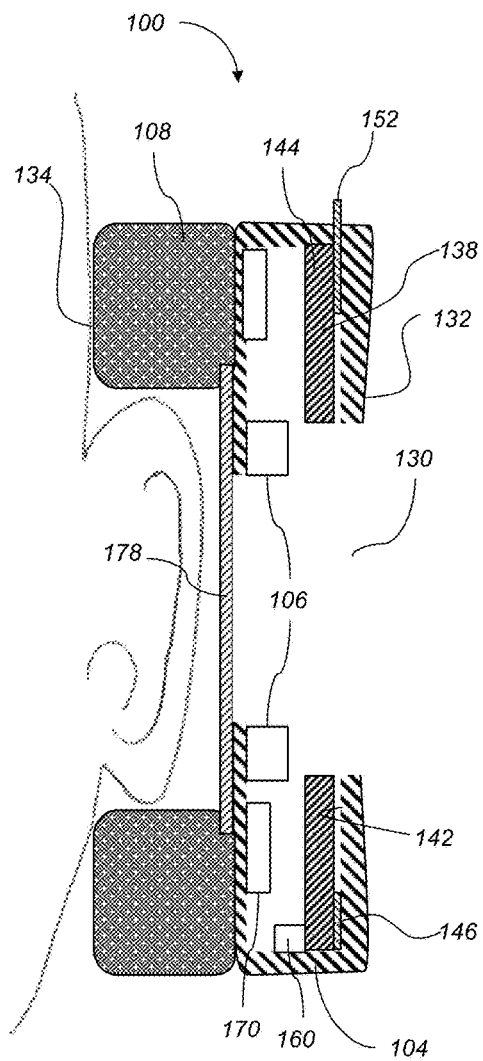
FIG. 3a illustrates a cross section view through section 3-3 in FIG. 1 where the headphone aperture is in an opened position.
Figure 3B:
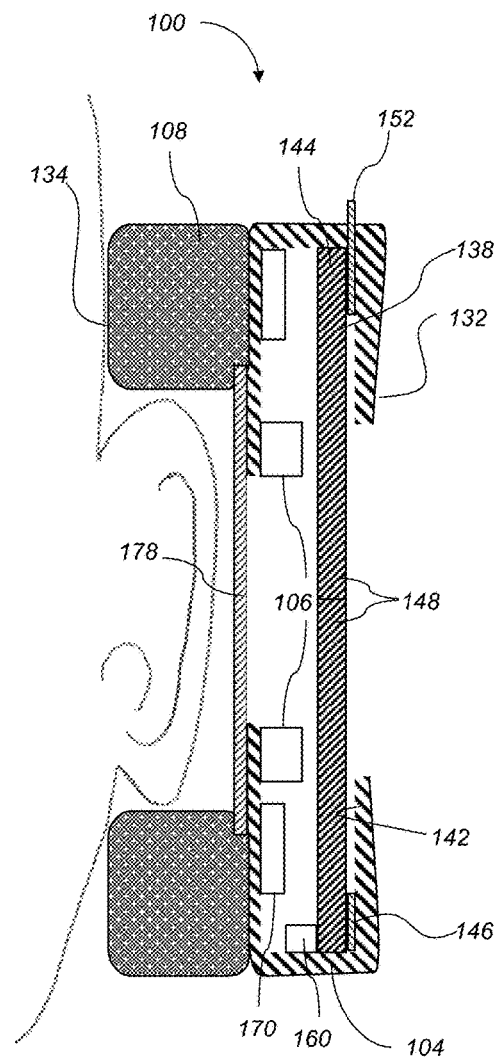
FIG. 3b illustrates a cross section view through section 3-3 in FIG. 1 where the headphone aperture is in a closed position.

As shown in FIGS. 3a-3b, the headphones 100 include an ear cushion 108 connected to the ear piece housing 104. The ear cushion 108 can be sized to fit on the wearer's ear or over the wearer's ear. In each case, ear cushion 108 is formed of resilient material adapted to seal and surround wearer's ear and form a chamber enclosing the wearer's ear in order block incoming sound. The ear cushion 108 may also be sized to seal on the wearer's ear, such as on in supra-aural headphones.

In one embodiment, the headphones 100 may be hearing protectors worn to block incoming sound. In another embodiment, the headphones 100 include an acoustic driver 106 (e.g., an acoustic transducer or speaker). In headphones 100 including an acoustic driver 106, the ear piece housing 104 and ear cushion 108 are arranged relative to the wearer's ear to direct audio signals output by the acoustic driver 106 toward the ear of the wearer.

As shown in FIG. 1, various aspects of headphones may include a yoke 112 disposed between the support member 102 and the ear piece housings 104. The ear piece housings 104 can pivot relative to the yoke 112 to enable a more comfortable fit for different wearers. The headphones 100 can include a cable 120 and a headphone jack 122 that can connect to a media player (e.g., an iPod®, a smart phone, or a tablet). The cable 120 can also include a microphone 126. If the headphones are connected to the wearer's smart phone, the microphone can enable the wearer to listen (via the acoustic drivers 106) and speak (via the microphone 126) to a telephone conversation, Skype® conversation, or the like. The headphones 100 can receive audio signals from the media player for the acoustic drivers 106 via the cable 120. The headphones 100 can also receive other types of data from the media player and send data, such as commands, to the media player via the cable 120. Various aspects of the headphones can omit the cable 120 and headphone jack 122 for a wireless connection (e.g., a Bluetooth® connection) to the media player.

In headphones that have ear cushions that seal well around the ear, while being effective at block incoming sound, the headphones may make the wearer's own voice muffled, and also get uncomfortably warm around the ear. In the case of hearing protection headphones, users do not want to wear the hearing protectors due to these drawbacks, even when damaging noise is possible. For example, hunters despite the loudness of gunshots when firing a gun, do not want to wear sealed hearing protectors while hunting because the headphones also acoustically isolate the hunter from environmental sounds, in addition to being uncomfortably warm and muffling their voice.

In an audio headphone with acoustic drivers, the ear cushions may be comfortable and provide excellent sound to the wearer, but the headphones may acoustically isolate the wearer from the surrounding environment. This can be problematic because the wearer may not be aware of important communications in their surrounding environment or warning signals.

Further, with audio headphones, users often experience the same audio content differently and different types of music are best enjoyed through different headphone configurations. In some instances there is a desire to have an open-back versus a closed-back in headphones, and vice versa, or, a partially open back. A closed back configuration that reinforces the bass may be desired for hip hop while an open back configuration may better present acoustic vocals. Also, when mixing, audio content producers often flip one of their headphone's cups off of their ear so that they can experience the sound as part of their surrounding environment.

To overcome these problems and allow various listening configurations, the headphone 100 has an adjustable aperture 130 formed on a back surface 132 of the housing 104. The back surface 132 is the surface of the earpiece housing 104 that is furthest from the wearer's ear at a distal end of the housing 104. The back surface 132 is opposite a contact surface 134 of the ear cushions 108 and may be generally parallel to the wearer's ear.

While the adjustable aperture 130 depicted in detail FIGS. 2a-2d consists of a number of interlocking blades 138 forming an adjustable shutter assembly 140 similar to the iris of a camera, a person of ordinary skill in the art would understand that other adjustable aperture designs may be employed and are within the scope of the present disclosure. For example, the shutter assembly may be formed like a Venetian or slat blind having a plurality of blades that are rotatable between the opened or closed position. In shutter assembly formed as a slat blind, the blades may be oriented vertically or horizontally and rotatable about a longitudinal axis of the blade. Similarly, the blades of the shutter assembly may be rectangular blades having a generally constant cross-section, or the blades may have any suitable shape for use in the shutter assembly.

The shutter assembly 140 shown in FIGS. 2a-2d includes a plurality of overlapping curved blades 138 mounted in a circle along a mounting surface 142 of the housing 104. The blades 138 can be rotated in unison to adjust the diameter of the aperture 130. The shutter assembly 140 includes a rotatable disk 146 provided with a corresponding aperture. A first end 144 of each of the blades 138 is mounted in a fixed pivotal position to either the rotatable disk 146 or the mounting surface 142. The second end 148 of the each blade is mounted in a sliding pivotal position to the other of the rotatable element or the mounting surface 142.

The blades 138 can be mounted at equal points around the circumference of the mounting surface, and are so shaped that inner edge 150 (FIG. 2a-2d) of each blade 138 has a curvature that corresponds to the curvature of the aperture 130 defined by the mounting surface 142. When the blades 138 move to the fully retracted position, the aperture 130 may be unobstructed by the blades 138, as shown in FIG. 3a. Various shapes and numbers of blades can be used to choose a predetermined curved or geometric shape as the aperture of the iris opens and closes when the mounting surface 142 and rotatable disk 146 are rotated relative to one another.

When the rotating disk 146 is rotated, each of the blades 138 is rotated about their fixed pivot point and extends to cover and close the aperture 130. The shutter assembly 140 moves the blades 138 from a fully open position, shown generally in FIG. 2a, to a fully closed position, shown in FIGS. 2d and 3b in approximately 110 degrees of rotation.

The rotatable disk 146 is positioned in a slot the housing 104, and it is provided with a protruding lever 152 that is accessible outside the housing 104 by the wearer. The lever 152 acts as a handle and allows the wearer to manually move the shutter assembly 140 between the opened and closed positions. As shown in FIG. 2a-2d, when the lever 152 is rotated in a circular direction. The lever 152 may extend beyond an outer surface of the housing 104 to be easily accessible, as shown in FIGS. 4a-4b. Any suitable handle and movement may be used to move the blades of the shutter assembly between the open and closed position.

In another embodiment, the headphone 100 includes an actuator 160 that is connected to the shutter assembly 140 to automatically move the shutter assembly 140 between the open and closed positions. The actuator 160 may include an electric motor, a piezoelectric element, a solenoid, or other suitable actuators for moving the shutter assembly between the open and closed positions.

Figure 4:
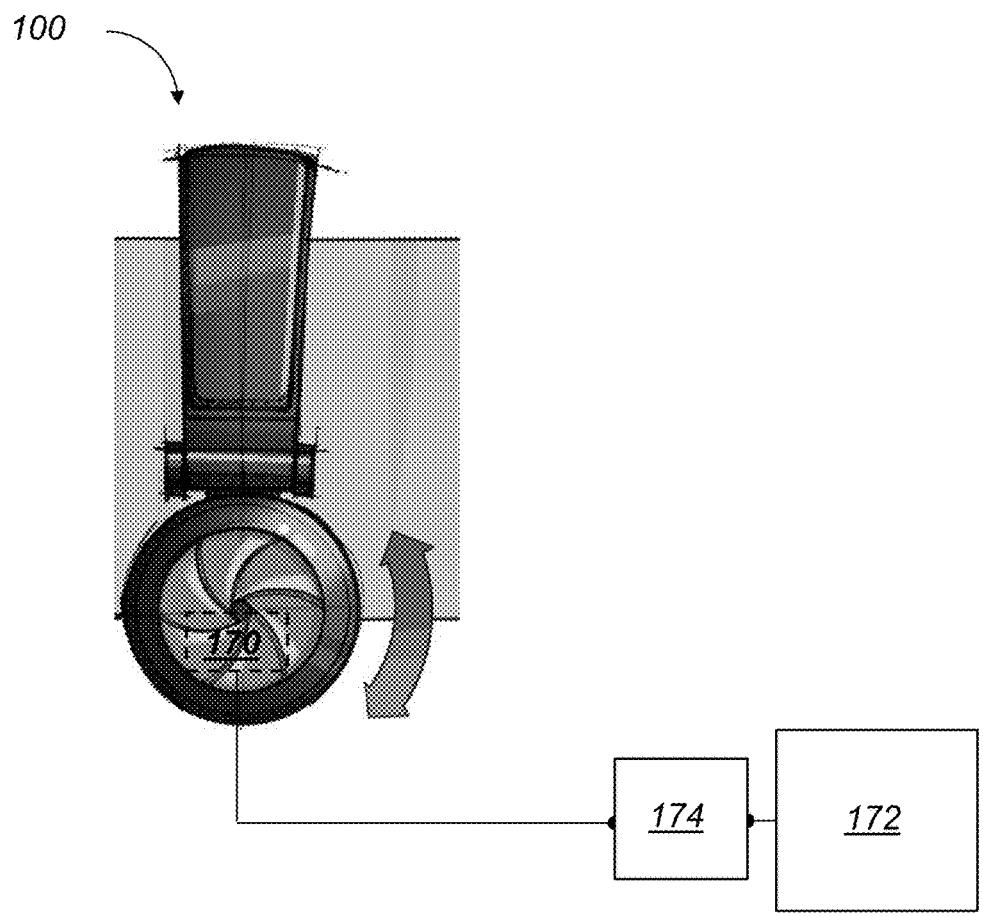
FIG. 4 illustrates a schematic headphone and external device configuration.

The headphone 100 may also include a controller 170 that is in communication with an external device 172 and/or a sensor 174, as shown in FIG. 4. While a wired connection is shown between the headphone 100 and external device 172 and a sensor 174, the connection could be a wireless signal, such as a Bluetooth signal.

In one embodiment, the external device may include a gun. Despite the loudness of gunshots, hunters may not always wear hearing protection in the field since hunters want to be able to hear sounds of prey approaching and it would not be convenient to put on hearing protectors before quickly firing their gun. In the embodiment where the external device is a gun, the sensor may be a tactile or capacitive sensor on the trigger of the gun, or on clothing of the wearer or perhaps on a separate device in communication with the gun. When the sensor 174 detects that a user is going to fire the gun, the sensor 174 provides a signal to the controller 170 to move the shutter assembly 140 to the closed position to protect the wearer from the damaging sound generated by the gunshot. The controller 170 provides a signal to the motor to automatically move the shutter assembly 140 to the closed position. When the sensor does not sense the gun is going to be fired, the controller 170 returns the shutter assembly 140 to the opened position.

To provide maximum hearing protection, such as for use with a gun, the blades 138 are adapted to make full contact and may even overlap with each other. To ensure that the blades 138 seal when moved to the closed position, the blades could be made of a firm rubber or coated with a rubber or silicone or other suitable material. Further, the blades 138 may also be at least as thick as the housing 104, for example, approximately 4 mm thick. However, the thickness of the housing and blades may vary depending on the materials or other design features of the headphones.

The headphones 100 may also include a sensor for sensing sound signals outside the housing. The sensor may include a microphone incorporated into the housing 104 or positioned external to the housing 104. The controller 170 may be programmed move the shutter assembly 140 in response to the volume, frequency, and/or duration of sound sensed outside the headphones 100. For example, the controller 170 may close the shutter assembly 140 sensor senses sound in excess of a predetermined threshold that may be damaging to the wearer's hearing. Alternatively, the controller 170 may open the shutter assembly 140 to the open position when the sensor senses an alarm or an emergency siren that the wearer should be aware of in an emergency situation.

In another embodiment, the external device 172 may include a phone, such as an office phone or mobile phone that is in communication with the headphones 100. If the wearer receives a phone call, the controller 170 receives a signal of the incoming call and automatically moves the shutter assembly 140 to the closed position before the wearer answers so that the caller can clearly hear the incoming call. When the call is completed, the controller 170 returns the shutter assembly 140 to the open position.

When the headphones 100 are being used as audio headphones with acoustic drivers 106, the controller 170 may also include an equalizer for controlling the sound generation by the acoustic drivers 106. The controller 170, via the equalizer, may increase the low frequency sound signals when the shutter assembly 140 is in the open position. Since bass sounds at low frequencies would be diminished when the shutter assembly 140 is open, the equalizer may restore at least a portion of the bass sounds using a low pass shelving filter.

The headphones 100 may also include a cover 178 disposed in the chamber. The cover 178 allows transmission of sound, but may shield the wearer's ear from the environment when the shutter assembly 140 is in the open position. The cover 178 may be formed of a thin membrane material. The cover 178 may be attached to the housing 104 along an interior surface, or may be sandwiched between the housing 104 and the ear cushions 108.

Figure 5:
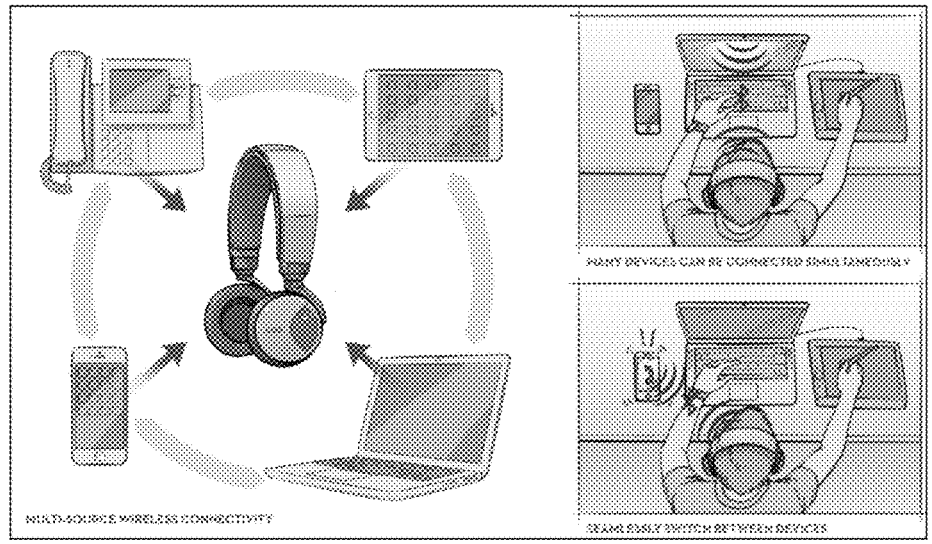
FIG. 5 illustrates a schematic view of headphones according to a second embodiment, including a view where the headphones are being worn by a user.
Figure 6:
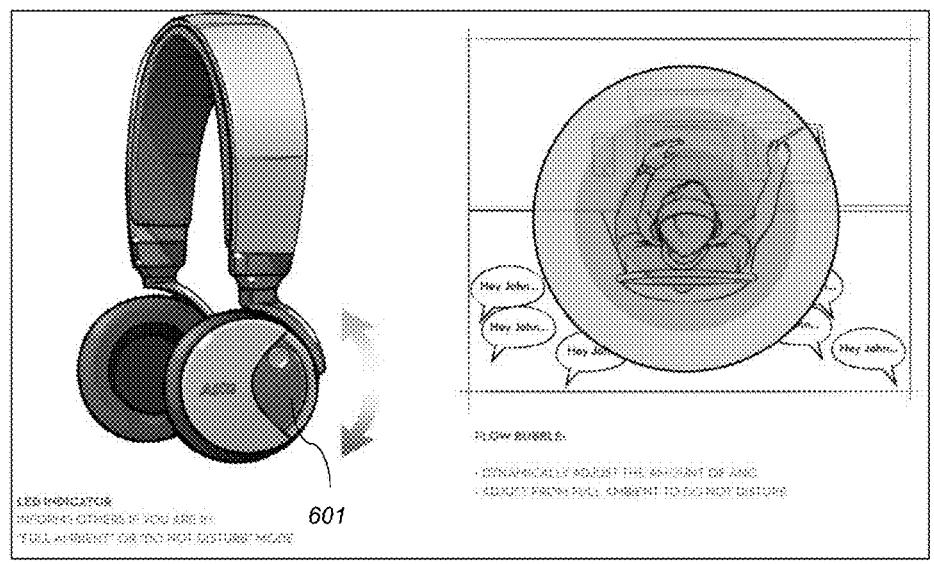
FIG. 6 illustrates a perspective view of the headphones of FIG. 5 in more detail.

FIGS. 5-6 illustrate another embodiment of the present disclosure. Currently, users are often inconvenienced by the inefficiencies of possessing and simultaneously monitoring or using multiple electronic devices. For instance, an office worker may be working on a laptop and using headphones to listen to audio. That user may, for instance, simultaneously have a smart phone, a tablet, and an office phone. If the user receives a phone call on their smart phone, they may need to remove their headphones, even if they include a microphone if that microphone is not in communication with their smart phone. If the user then receives a phone call to their office phone simultaneously, they must struggle to balance the call on their smart phone with the new incoming call. Such disorganization is inefficient and disrupts a user's work flow in a highly negative way. Further, even though some headphones are adept at noise canceling low-frequency noises, such as constant ambient sounds, high-frequency sounds such as the voices of surrounding individuals are not blocked.

Disclosed is a headphone set that allows a user to simultaneously manage a plurality of devices. In certain embodiments, the headphones are in wireless electronic communication with multiple devices. Those of skill in the art of the present disclosure will appreciate that various communication technologies, such as Bluetooth and Wi-Fi, may be employed to accomplish this communication. In some instances, wired connections may also be employed. Software manages and prioritizes the devices accordingly to criteria, which are preferably selected by the user.

In certain alternative embodiments, connections are made between various devices and a dongle, which may for instance rest on a user's desk. In such embodiments, communication functionality and processing may be supported by wired connections to some of the devices, with wireless communication being made to other devices.

Optionally, a user can control various functions and prioritization via controls included in the headphones or via an app on a mobile device.

In certain embodiments, the headphones incorporate an indicator, such as a green/red light to indicate to individuals around them whether user wishes to remain isolated. Optionally, the headphones may incorporate ambient noise canceling of either or both high and low frequency noises by physical manipulation of a portion of the head phone, such as rotation of portion 601 in FIG. 6. A user thus may selectively cancel none of the surrounding noise, only ambient sounds, or nearly all sound so as to create a near total sound bubble in which to remain isolated.

Figure 7:
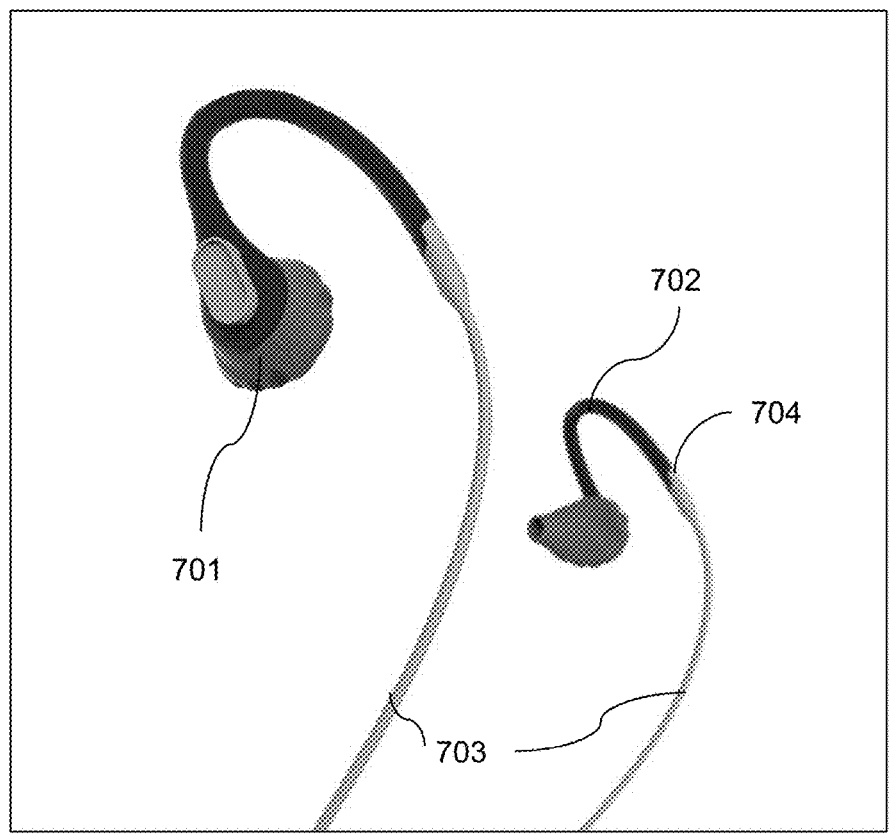
FIG. 7 illustrates a perspective view of headphones according to a third embodiment.
Figure 8:
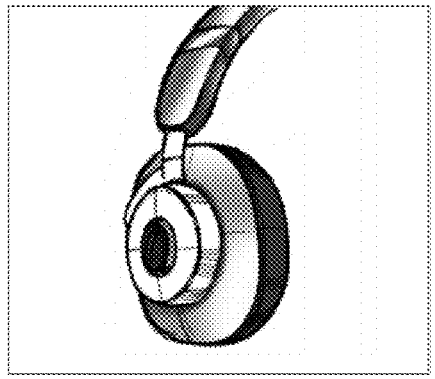
FIG. 8 illustrates a perspective view of headphones according to a fourth embodiment.

FIG. 7 illustrates another embodiment of the present disclosure. Often, individuals who are exercising use headphones so that they can listen to audio, typically music. In many instances, such individuals may employ traditional wired earphones or ear buds. While dependable in that they do not require batteries, they require a wired connection to an audio device, such as a smart phone, in order to operate. Such wires are ungainly, difficult to size to particular users, and are prone to snagging on various objects. This can lead to separation of the headphones from the audio device, destruction of the ear phones and other inconvenient or even dangerous situations. Furthermore, often users only employ one of the two included earphones so that they can, for instance, hear and interact with their surroundings. This leaves the second earphone dangling from the user's body, which is inconvenient and presents another wire to be snagged.

There are existing wireless ear phones that connect to an audio device, for instance via Bluetooth. While such designs eliminate the need for wires and their attendant problems, they introduce new challenges. Primarily, such designs require a battery that must be charged in order to operate. Many individuals forget to charge the units or do not wish to be inconvenienced in needing to do so whenever they wish to use their headphones.

With reference to FIG. 7, disclosed are wireless earphones, each which may be selectably coupled with a common wire for connection to an audio device.

Earphones 701 and 702 connect to wire 703. In one embodiment, such connection is accomplished via magnetic connection 704. Therefore, the user may select whether or not to operate the earphones in a wired or wireless configuration. For instance, if a user is not moving and does not wish to drain their earphones' batteries, they may have the earphones connected to the wire, which is plugged into the audio device. Various configurations may be used for connection to an audio device, without limitation including 3.5 mm audio jacks or micro-USB connectors. This may allow a user to, in some embodiments, charge the earphones. Otherwise, connection will stop battery drain. Once a user wishes to be more active, they may disconnect the cable and connect the earphones to the audio device wirelessly. An internal microphone may be incorporated for making phone calls.

In certain embodiments, a user can choose to employ only one of the earphones. In this scenario, the audio device may include software for conditioning the audio media to better work with the single earphone. If the user is employing both earphones, they may hand one to a friend to listen to, allowing them to partake in the audio. Thus, the user is empowered in various usage situations to select which earphone setup they wish to employ.

FIGS. 8-11 illustrate another embodiment of the present disclosure. In many instances, users have a number of audio devices that they employ in a typical day. For instance, a user may have a set of ear covering headphones to listen to high quality audio and also to isolate themselves from their surrounding environment. Separately, the same user may frequently employ a Bluetooth-connected ear piece for making calls while still being able to interact with their surrounding environment. Carrying and charging multiple such devices can be cumbersome, time consuming, and disruptive to one's work flow.

Figure 9:
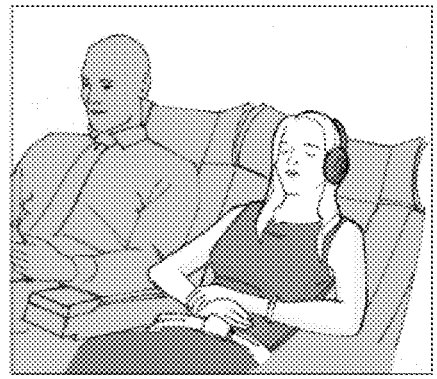
FIG. 9 illustrates the headphones according of FIG. 8 where the headphones are being worn by a user.
Figure 10:
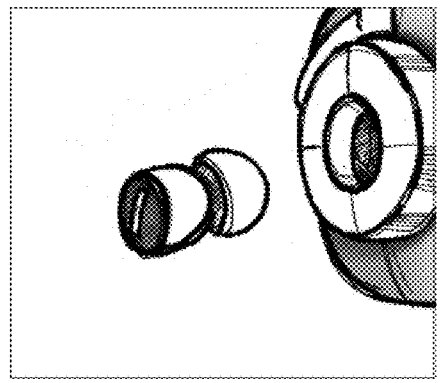
FIG. 10 illustrates an exploded view of the headphones according of FIG. 8.
Figure 11:
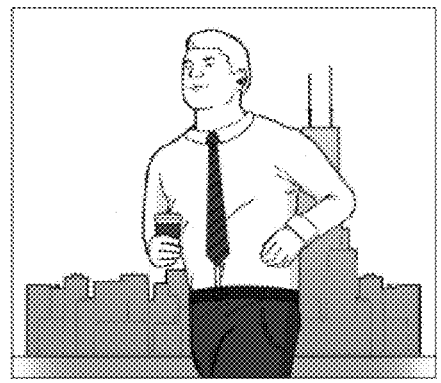
FIG. 11 illustrates a portion of the headphones of FIG. 8 being worn by a user.

Disclosed is a paired headphones set and single ear bud Bluetooth device. In a first configuration, the headphones act as a typical headphone set, allowing a user to isolate themselves from their surroundings, as depicted in FIG. 9. In a second configuration, the user may remove the ear bud and use it as a Bluetooth device independent of the headphone set. When coupled with the headphones, the headphones serve to charge the ear bud. The ear bud may incorporate a microphone allowing it to be used with telephone calls.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A headphone comprising:
   a headphone housing;
   a resilient cushion attached to the housing defining a chamber with the housing for enclosing the user's ear;
   an assembly disposed in the housing proximate to a distal end and having a plurality of blades, each of the plurality of blades moveable between at least one open position and a closed position, wherein in the closed position, the plurality of blades interlock with each other to define a distal surface of the housing, and in the open position, the plurality of blades define an aperture in the housing, wherein the aperture allows sound communication from outside the housing into the chamber; and
   a controller in communication with the assembly and at least one external device, wherein the controller is programmed to:
   receive a signal from the external device
   command the assembly to move between the open position and the closed position based on the signal.

2. The headphone of claim 1 wherein the external device comprises a gun and the signal is indicative that the user is going to fire the gun, wherein the controller moves the plurality of blades to the closed position before the user fires the gun.

3. The headphone of claim 2 wherein the actuator comprises an electric motor connected to the assembly.

4. The headphone of claim 1 further comprising at least one acoustic driver for transmitting sound signals to the chamber in the headphone.

5. The headphone of claim 4 wherein the controller includes an equalizer in communication with the acoustic driver, wherein the equalizer increases low frequency sound signals when the assembly is in the open position.

6. The headphone of claim 4 wherein the external device comprises a phone and the signal is indicative of an incoming call, wherein the controller moves the plurality of blades to the closed position and turns off the acoustic driver.

7. The headphone of claim 1 further comprising an actuator connected to assembly for moving the plurality of blades between the open and closed position.

8. The headphone of claim 1 wherein the assembly includes a rotating disk connected to housing and the plurality of blades, wherein rotation of the disk with respect to the housing moves the assembly between the open and closed position.

9. The headphone of claim 1 wherein the external device comprises a microphone and the signal is indicative of an alarm, wherein the controller moves the plurality of blades to the open position based on the signal.

10. A method comprising:
    providing a headphone housing having an assembly having a plurality of blades, each of the plurality of blades moveable between at least one open position and a closed position, wherein in the closed position, the plurality of blades interlock with each other to define a distal surface of the housing, and in the open position, the plurality of blades define an aperture in the housing, wherein the aperture allows sound communication from outside the housing into the chamber;
    receiving a signal from an external device;
    moving the assembly between the open position and closed position based on the signal.

11. The method of claim 10 further comprising moving the plurality of blades to the closed position when the signal is indicative that the user is going to fire a gun.

12. The method of claim 11 further comprising receiving a signal from a sensor disposed on a trigger of the gun.

13. The method of claim 10 further comprising moving the plurality of blades to the closed position when the signal is indicative of an incoming call.

14. The method of claim 10 further comprising increasing low frequency sound signals by an acoustic driver via an equalizing filter when the plurality of blades are in the open position.

15. The method of claim 10 further comprising providing an instruction to an actuator connected to assembly to moving the plurality of blades between the open and closed position.

16. The method of claim 10 further comprising moving the plurality of blades to the open position when the signal is indicative of an alarm.

17. A headphone comprising:
    a headphone housing;
    a resilient cushion attached to the housing defining a chamber with the housing for enclosing the user's ear; and
    an assembly disposed in the housing proximate to a distal end and having a plurality of blades, each of the plurality of blades moveable between at least one open position and a closed position, wherein in the closed position, the plurality of blades interlock with each other to define a distal surface of the housing, and in the open position, the plurality of blades define an aperture in the housing, wherein the aperture allows sound communication from outside the housing into the chamber.

18. The headphone of claim 17 further comprising a handle operable by the user outside the housing for moving the plurality of blades between the open and closed position.

19. The headphone of claim 18 wherein the assembly includes a rotating disk connected to handle and the plurality of blades, wherein rotation of the disk with respect to the housing moves the plurality of blades between the open and closed position, wherein operation of the handle moves the rotating disk.

20. The headphone of claim 17 further comprising at least one acoustic driver for transmitting sound signals to the chamber in the headphone.

* * * * *